(12) United States Patent
Morrison, Jr. et al.

(10) Patent No.: US 8,301,401 B2
(45) Date of Patent: Oct. 30, 2012

(54) LOW PROFILE ENCIRCLING ULTRASONIC PROBE FOR THE INSPECTION OF IN-SITU PIPING IN IMMERSION MODE

(75) Inventors: Donald W. Morrison, Jr., Madison Heights, VA (US); Daniel T. MacLauchlan, Lynchburg, VA (US); William C. Rutherford, Madison Heights, VA (US); Todd E. Mitton, Cambridge (CA)

(73) Assignees: Babcock & Wilcox Technical Services Group, Inc.; Babcock & Wilcox Canada Ltd.

( * ) Notice: Subject to any disclaimer, the term of this patent is extended or adjusted under 35 U.S.C. 154(b) by 240 days.

(21) Appl. No.: 12/873,082

(22) Filed: Aug. 31, 2010

(65) Prior Publication Data

US 2012/0053856 A1    Mar. 1, 2012

(51) Int. Cl.
*G01B 17/00* (2006.01)
(52) U.S. Cl. ............... 702/39; 702/34; 702/35; 73/600; 73/618

(58) Field of Classification Search ............ 702/34, 702/35, 39; 73/598, 600, 618–620, 622, 73/633, 634, 640, 641, 644
See application file for complete search history.

(56) References Cited

U.S. PATENT DOCUMENTS

| 7,694,569 | B2 * | 4/2010 | McGrath et al. | 73/644 |
| 7,823,454 | B2 * | 11/2010 | MacLauchlan et al. | 73/618 |
| 2012/0067129 | A1 * | 3/2012 | Fujiwara et al. | 73/644 |

* cited by examiner

*Primary Examiner* — Sujoy Kundu
(74) *Attorney, Agent, or Firm* — Eric Marich; Mike Seymour

(57) ABSTRACT

An ultrasonic probe encircles the perimeter of a target component to be ultrasonically tested and has a base and a pair of jaws pivotally mounted to the base at opposite ends of an arcuate inner surface of the base to encircle a target component with arcuate inner surfaces of the jaws as well. The inner surfaces form a coupling fluid chamber with an outer surface of the target component. Front and rear sets of seals connected to and extending along front and rear portions of the arcuate inner surfaces seal the chamber so that it can retain a coupling fluid such as water. An arcuate set of ultrasonic transducers is connected along at least one but preferably all of the arcuate inner surfaces for transmitting ultrasonic signals to the coupling fluid chamber and into the target component.

20 Claims, 9 Drawing Sheets

Time delays

Half Amplitude Beam Profile

Time delays

LEGEND FOR FIGS. 14-17

ULTRASONIC WAVE PEAK INTENSITY ("ENERGY")
1.0 = NORMALIZED MAXIMUM AMPLITUDE

| AMPLITUDE RANGE | GRAPHCAL REPRESENTATION IN FIGURE |
|---|---|
| 1.0 – 0.707 |  |
| 0.707 – 0.5 |  |
| 0.5 – 0.355 |  |
| 0.355 – 0.0 |  |

LOW PROFILE ENCIRCLING ULTRASONIC PROBE FOR THE INSPECTION OF IN-SITU PIPING IN IMMERSION MODE

FIELD AND BACKGROUND OF THE INVENTION

1. Field of the Invention

The present invention relates generally to the field of non-destructive testing, and in particular to a new and useful ultrasonic probe having a pipe-encircling, low profile configuration for the onsite inspection of pipes.

2. Description of the Related Art

The CANadian Deuterium Uranium or CANDU reactor contains complex arrays of pipes. One of these arrays is shown in part in FIG. 11. The pipes of these arrays must be tested onsite (in-situ) at various times during the life of the reactor. Because of the complex nature and close spacing of the CANDU pipe arrays, access to the pipes for testing is difficult.

Corrosion, erosion, and cracking are problems in industrial piping that can be detected by ultrasound (UT). For inspections, sound is generated by a transducer and sent into a target component. The reflections, or echoes, from the generated sound are then received after exiting the component and used to detect defects. As transmission of ultrasound through air into a typical test component is less than ideal, the inspecting transducer(s) should be coupled to the target component by a material that allows a significant portion of the sound to be transmitted into the component. Typically field inspections are done in contact by attaching a plastic shoe or wedge in between the transducer and the target component. The plastic is generally constructed to match the shape of the target component, and a coupling medium, such as gel or water, of thickness less than one wavelength is used at the plastic-to-metal interface to minimize air gaps. This method tends to work well if the target component is smooth and of known geometry. If the surface of the component is non-uniform or the component has geometry changes such as elbows or welds, then the plastic shoe can lift off the surface of the component and cause loss of signal.

Immersion ultrasonic testing is typically performed in a laboratory or production environment where an immersion tank can be used and has many advantages over contact ultrasonic testing but is not well adapted to onsite testing.

A need exists for a low profile, on-site, UT pipe tester that is capable of accessing and testing the pipes in a complex array.

SUMMARY OF THE INVENTION

It is an object of the present invention to provide an ultrasonic probe having a pipe-encircling, low profile configuration for the onsite UT inspection of pipes or other target components that can be encircled by the probe.

The probe of the invention uses water for immersion testing as the only coupling medium with the in-situ pipe to be tested, and a gap between the transducer elements and the test component is much larger than a wavelength. This eliminates liftoff problems (associated with contact testing) and gives the probe the ability to scan past irregular geometry. This also gives the probe the ability to scan a larger area with more reliable data and less need to rescan.

The probe of the invention encircles the entire pipe to be tested with overlapping transducer arrays so that scan times can be greatly reduced. The ultrasonic beam can be scanned electronically in the circumferential direction eliminating the need to mechanically raster scan. Overlapping the arrays allows for continuous electronic scanning coverage without the need to precisely locate array segments with respect to each other. Using a phased array type system having 360 degree coverage also allows for multi-focus point scan data and therefore provides enhanced defect detection and definition.

A clamshell, hinged design with a low profile for much of the probe also allows the probe to inspect piping with limited clearance, for example, CANDU feeder pipes typically having only 0.5" to 2.0" of clearance in the radial direction.

An important purpose of the invention is to provide overlapping coverage around the entire circumference of in-service piping using immersion ultrasonic testing. The probe will be of clamshell design with twin joints and integrated seals. The hinged clamshell design is for supporting installation around existing piping. Each section of the clamshell will contain its own array of transducer elements. When closed, the arrays will overlap in the circumferential direction. The overlapping region will be sized to contain at least the number of elements needed to form the desired ultrasonic beam using phased array or an equivalent method. Each array will be able to operate independently.

Couplant, which may be water, is pumped into the probe and captured by probe seals to form an annular column between transducer elements in the probe and the pipe or target component being tested. The seals are flexible; e.g. of extruded elastomer, and compressed onto the pipe and onto any welds or other small irregularities on the pipe surface. The seals are thus constructed to seal over a range of changes in the radial direction. This will allow the probe to be moved radially and scan past regions of ovality, welds, and elbows without losing signal. Vacuum lines can be used to aid in evacuating air trapped by the probe, and for maintaining a reliable column of water.

Accordingly another aspect of the invention is drawn to an ultrasonic probe that encircles the perimeter of a target component to be ultrasonically tested and that has a base and a pair of jaws pivotally mounted to the base at opposite ends of an arcuate inner surface of the base to encircle a target component with arcuate inner surfaces of the jaws as well. The inner surfaces form a coupling fluid chamber with an outer surface of the target component. Front and rear sets of seals connected to and extending along front and rear portions of the arcuate inner surfaces seal the chamber so that it can retain a coupling fluid such as water. An arcuate set of ultrasonic transducers is connected along at least one but preferably all of the arcuate inner surfaces for transmitting ultrasonic signals to the coupling fluid chamber and into the target component.

The various features of novelty which characterize the invention are pointed out with particularity in the claims annexed to and forming a part of this disclosure. For a better understanding of the invention, its operating advantages, and specific benefits attained by its uses, reference is made to the accompanying drawings and descriptive matter in which a preferred embodiment of the invention is illustrated.

BRIEF DESCRIPTION OF THE DRAWINGS

In the drawings:

FIGS. 12 and 13 are schematic diagrams showing an inspection concept for use with the probe of the invention, FIG. 12 illustrating electronic scanning using 3.5 skips, while FIG. 13 illustrates the overlapping arrays;

DESCRIPTION OF THE PREFERRED EMBODIMENTS

Figure 1:
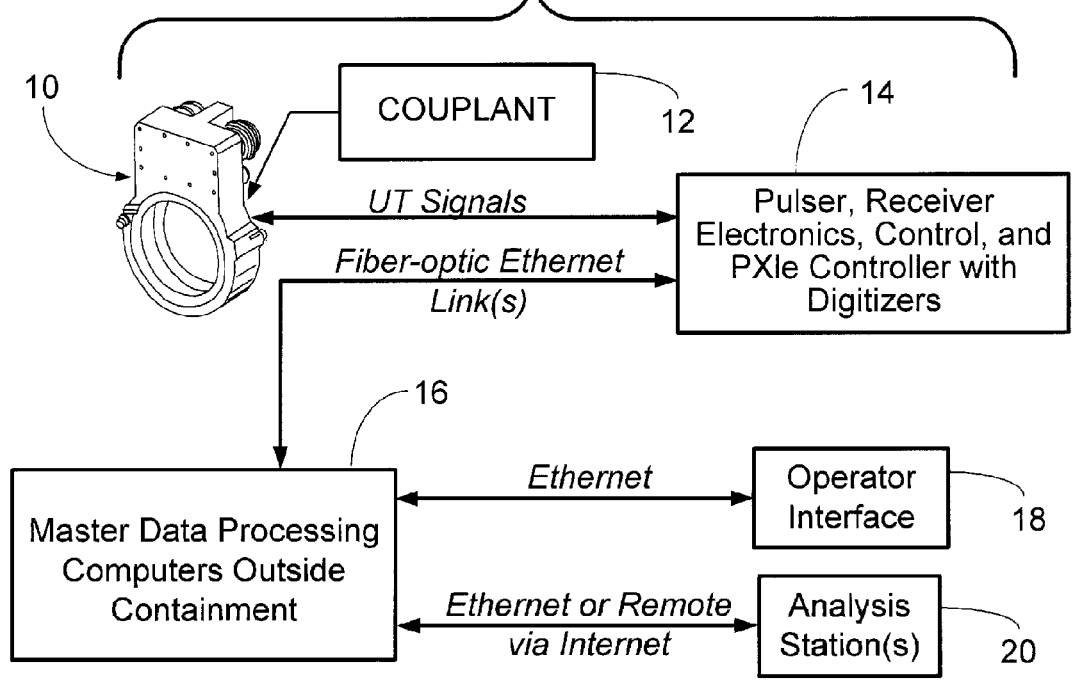
FIG. 1 is a diagram of a system for using the probe of the invention.

Referring now to the drawings, in which like reference numerals are used to refer to the same or similar elements, FIG. 1 shows an example of a system that can use the probe 10 of the invention, the system including a hydraulic component 12 for supplying couplant (preferably water) to the probe 10, pulser/receiver electronics 14 for sending and receiving ultrasonic signals to and from the probe UT transducers, master data processing computers 16 for processing the UT signals, and operator and analysis workstations 18 and 20 for inputting UT tests on target components and analyzing the results of those UT tests. Alternatively, commercially available systems such as OmniScan or TomoScan systems available from Olympus Corporation could be used.

Figure 2:
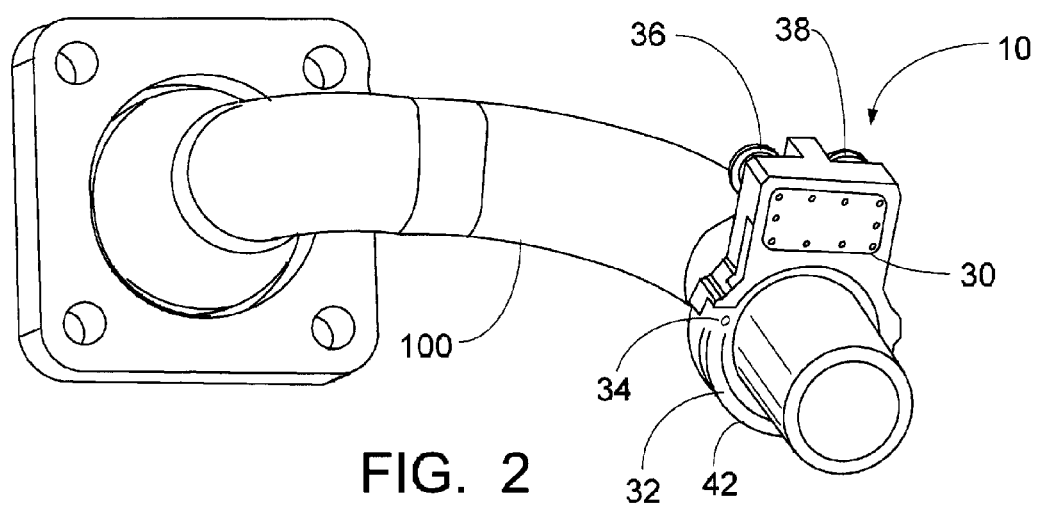
FIG. 2 is a perspective view of the probe of the invention in a closed and liquid sealing position encircling an onsite pipe to be UT tested.

In FIG. 2, probe 10 is shown to have a base 30 and a pair of jaws that are closed around and encircle a target component such as a pipe 100 to be UT tested. Each of the jaws 32 is pivotally connected to the base 30 at a joint or pivot hinge 34 that, like the base 30, carry two inwardly facing sets of seals that are pressed against the outer surface of the pipe when the jaws are closed to create an annular coupling fluid chamber between the inner surface of the probe 10, and the outer surface of the pipe 100 to provide in-situ, on-site immersion testing of the workpiece. Of the two seal sets, only the front seal set 42 is visible in FIG. 2. Strain relief connections 36 and 38 are connected to the base 30 for connecting the UT data cables (not shown) to the probe 10. Hydraulic connections (not shown in FIG. 2; see FIGS. 3, 4 and 7) are provided on the rear of the probe 10 for introduction of the couplant into the annular chamber of the probe 10. The couplant is either allowed to escape past the seals and/or returned to the couplant delivery system via vacuum lines (also not shown).

Figure 3:
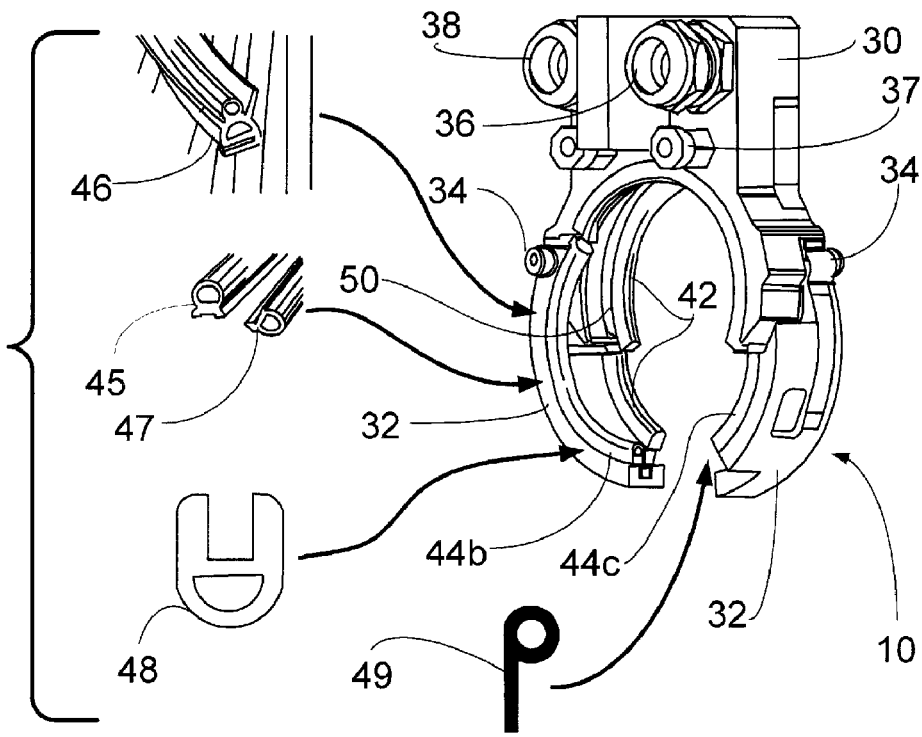
FIG. 3 is a rear perspective view of the probe with both of its jaws partly open and details of some of its seal options for sealing a liquid space around a pipe to be tested.

Turning to FIG. 3, the front seal set 42 as well as a rear seal set 44 are shown with both jaws 32, 32 in their partly open position. In order to engage the probe 10 around a pipe or other target component or workpiece, the jaws are opened further until the space between the lower ends of the jaws are farther apart than the diameter of the pipe and the probe is then moved to receive the pipe in the interior of the probe space defined below the base 30 and between the jaws 32, 32. Various seal cross sections can be used for the seals of the front and rear seal sets 42 and 44, some of which are illustrated at 45, 46, 47 and 48. In the alternative a sealing brush 49 can be used. The primary requirement is that the seals can accommodate and seal around any small imperfections or irregularities of the pipe circumference and that the coupling fluid is retained in the coupling chamber long enough for the UT testing to be performed. Accordingly a perfect seal is not necessary.

Figure 4:
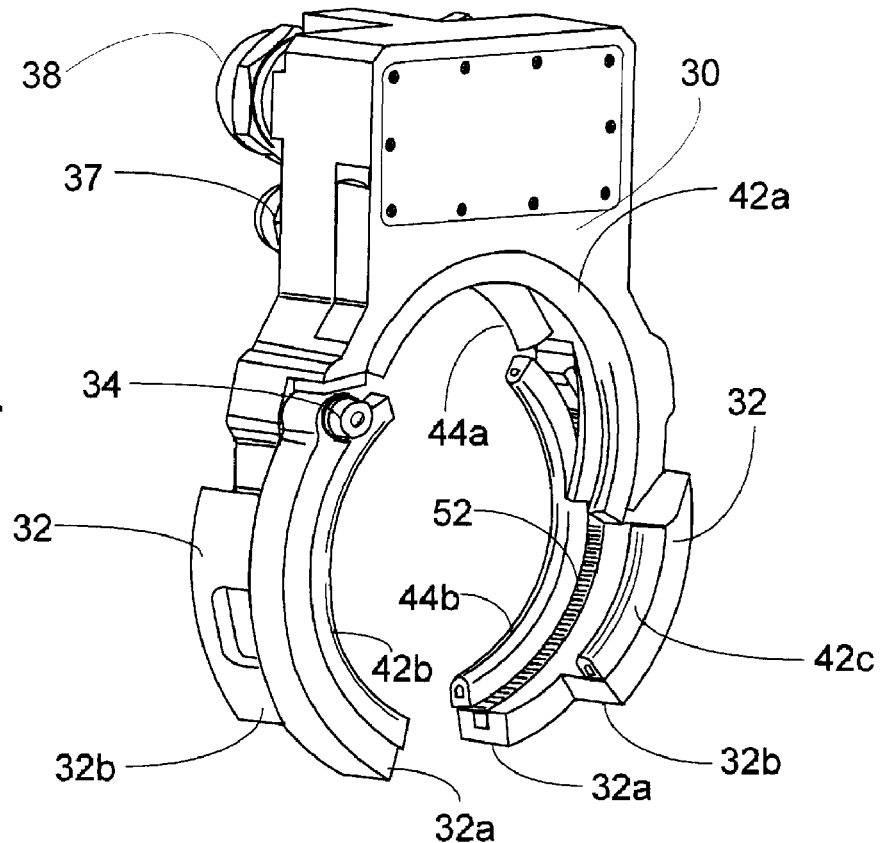
FIG. 4 is a front perspective view of the probe with both jaws in partly open positions.

FIG. 3 also illustrates where one of the arc shaped sets of UT transducers 50 can be placed, namely along the inside circumference of the arcuate inner surface of the base 30. FIG. 4 illustrates an arc shaped set of UT transducers 52 placed along the inside circumference of the arcuate inner surface of one of the jaws 32. Although only one UT transducer 50, or 52 is needed at a minimum, advantageously there is a transducer 50 on the base 30 and on both of the jaws 32 to maximize UT testing options with respect to the types of tests that can be performed, and in a manner that is independent of the relative circumferential orientation of the probe 10 with respect to the pipe; e.g. in cases when the pipe array is so crowded as to allow the probe to approach the pipe only from a certain direction. Couplant inlets 37 are also provided on base 30 for providing couplant to the probe 10.

FIG. 4 also illustrates how each jaw 32 has a long arcuate side 32a and a short arcuate side 32b, each carrying inwardly facing and respective long, front and rear seals 42b, 44b, and short, front and rear seals 42c and 44c. The front and rear seal sets 42 and 44 are each completed when the jaws are closed, by respective spaced apart front and rear seals 42a and 44a, on the arcuate inner surface of base 30.

Figure 5:
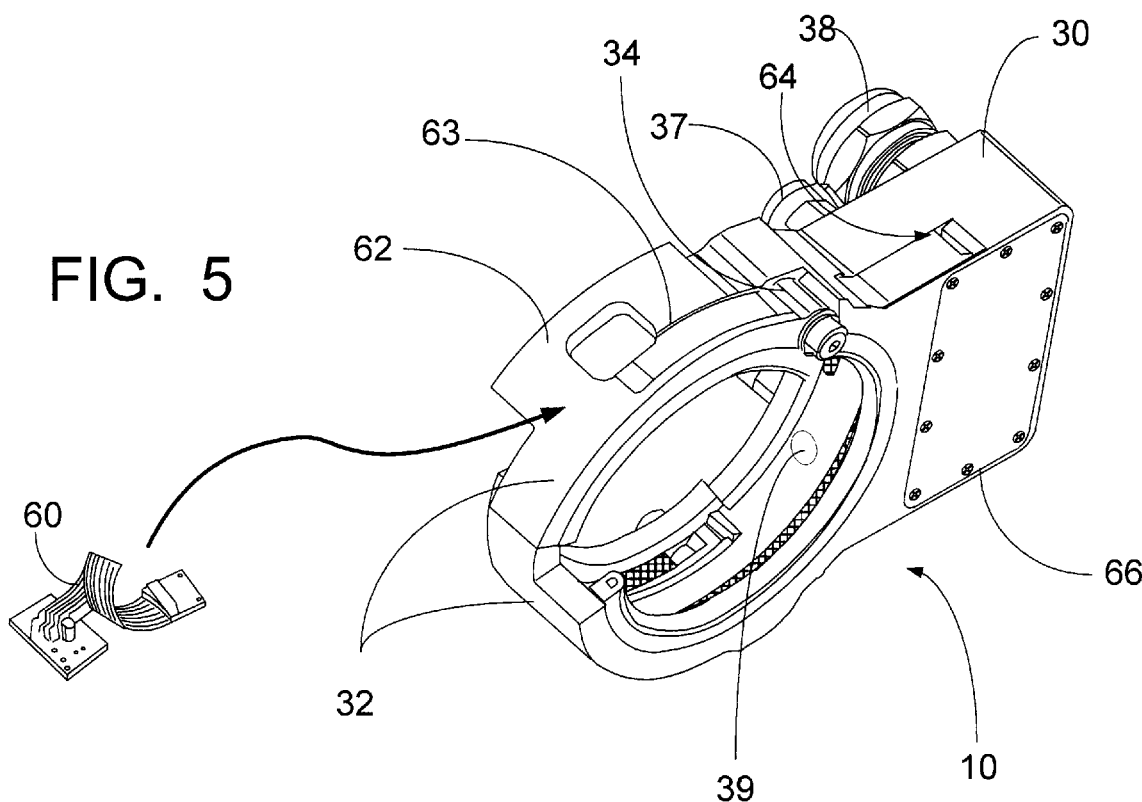
FIG. 5 is a front left side perspective view of the probe and an example of a proposed flexible circuit for the probe before it is installed, the probe having one jaw closed and the other partly open.
Figure 11:
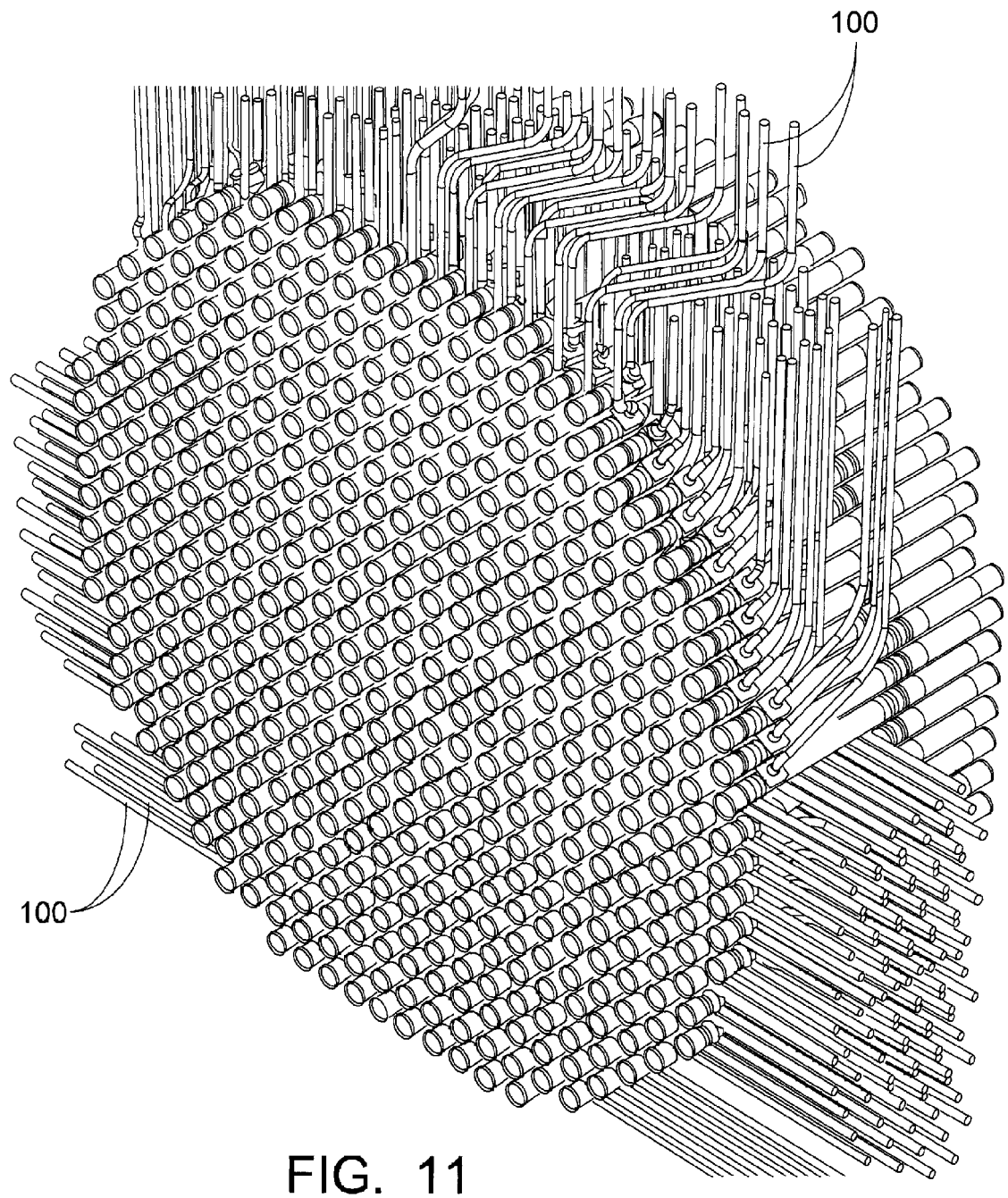
FIG. 11 is a partial perspective view of an array of feeder pipes of the CANDU reactor that can be tested using the probe of the invention.

All electrical connections are gathered on one side of the probe 10; i.e. at the top of base 30 as shown in FIG. 5, so that the rest of the probe can be low profile to aid in inspecting piping with low radial clearance such as CANDU feeder tubes shown in FIG. 11. This is accomplished by using flex circuits 60 to carry the signals across the hinged joints 34. These flex circuits 60 are potted in a recess 62 in each jaw 32 and are connected by being pulled tight across an area 63, even when the probe jaws are close, to a circuit board inside an electronic enclosure 64 that is integrated into the base 30 of the probe 10. Cables are soldered to the circuit boards and then passed through the strain reliefs 38 to be connected to the ultrasonic testing instrument 14 shown in FIG. 1. A cover plate 66 covers the electronics on base 30.

The coupling fluid inlet 39 opens into the annular coupling fluid chamber formed by the front and rear seal sets 42, 44, the arcuate inner surfaces of the probe 10 and the outer surface of the target component being tested, are also visible in FIG. 5. Supply couplant, such as water, provided to fitting 37 is preferably degassed upstream of probe 10 by a couplant delivery system (not shown). The positive pressure, available flow is supplied to the fitting 37 of probe 10. Suction lines can be used to aid in removing air.

Figures 6, 7:
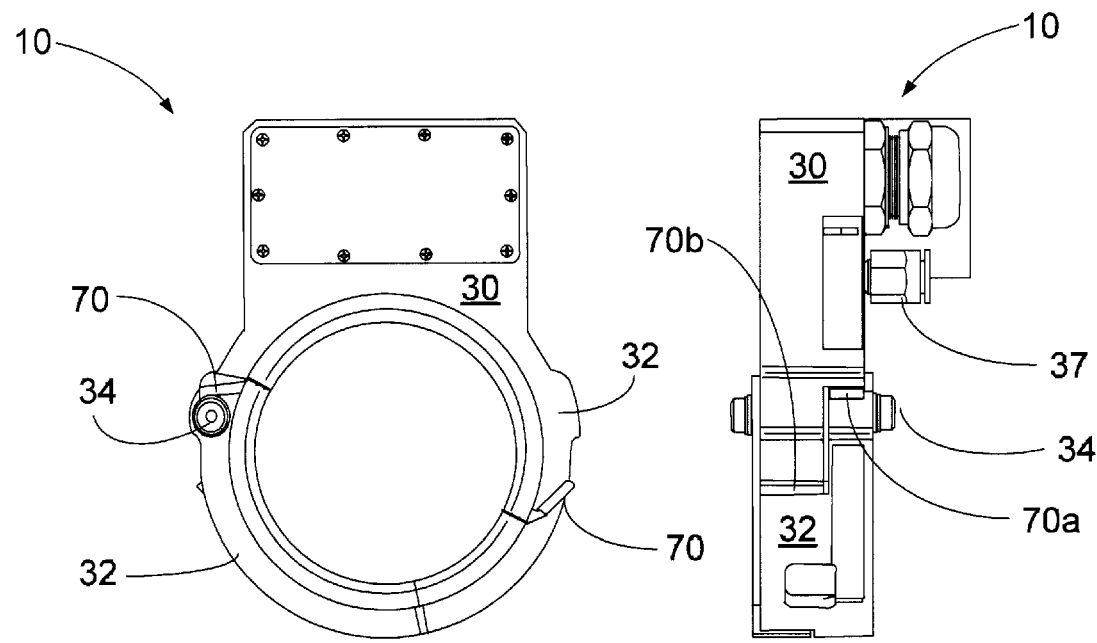
FIG. 6 is a front elevational view of the probe in its closed position and with examples of dimensions shown in inches.
FIG. 7 is a left side elevational view of the probe in its closed position and with examples of dimensions shown in inches.
Figure 8:
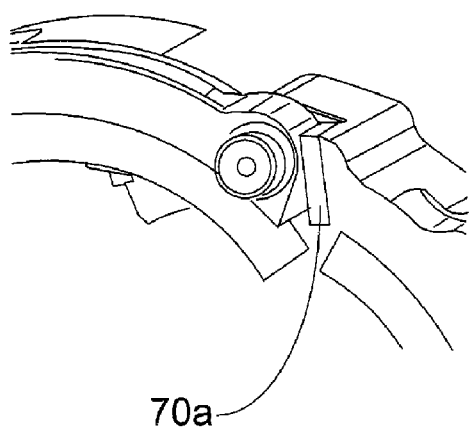
FIGS. 8, 9 and 10 are each partial perspective views of the joint area that is typical for the jaws of the probe, to illustrate the sealing arrangement for the joints of both jaws.
Figure 9:
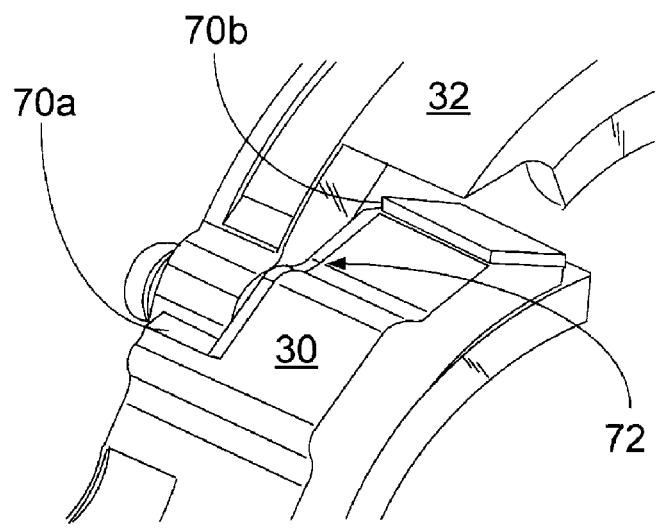
Figure 10:
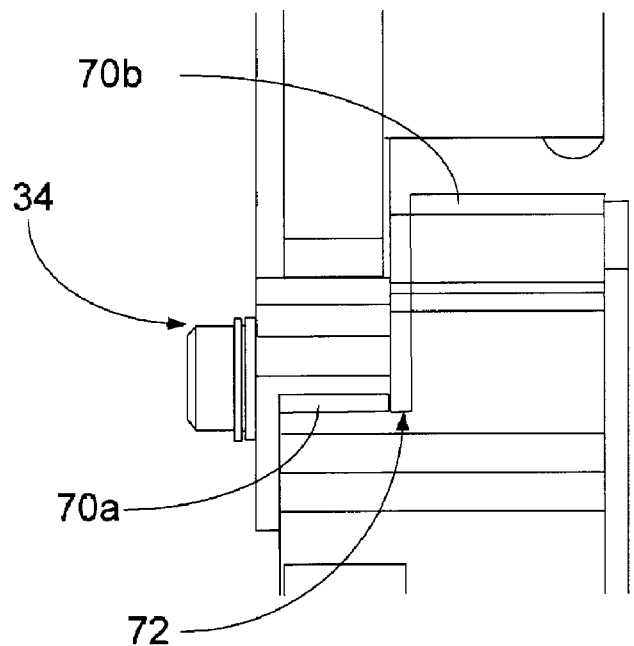

Referring to FIGS. 6 and 7, since the seal sets 42 and 44 are not continuous the two sides 32a and 32b of each jaw 32 are of different lengths, the short side 32b not reaching the joint 34, joint seals 70 are also needed at each joint. Each joint seal comprises a first gasket 70a for sealing the surfaces between the long jaw side 32a and the joint 34, and a second gasket 70b for sealing the surfaces between the short jaw side 32b and the joint 34. As shown in FIG. 8, there is also a slide surface seal 72 for creating a sliding seal on the jaw surface between the long and short sides of each jaw, and the side surface of the base 30 in the area of each joint 34. Each sliding seal is preferably made of a low friction elastic material such as ultra-high-molecular-weight (UHMW) polyethylene, and the seals of seal sets 42 and 44 and the gaskets 70 can be made of latex, silicone rubber or other suitable elastic, compressible material. Joints 34 are preferably made of sleeve bearings, SS shoulder bolts, and Belleville washers.

Figure 12:
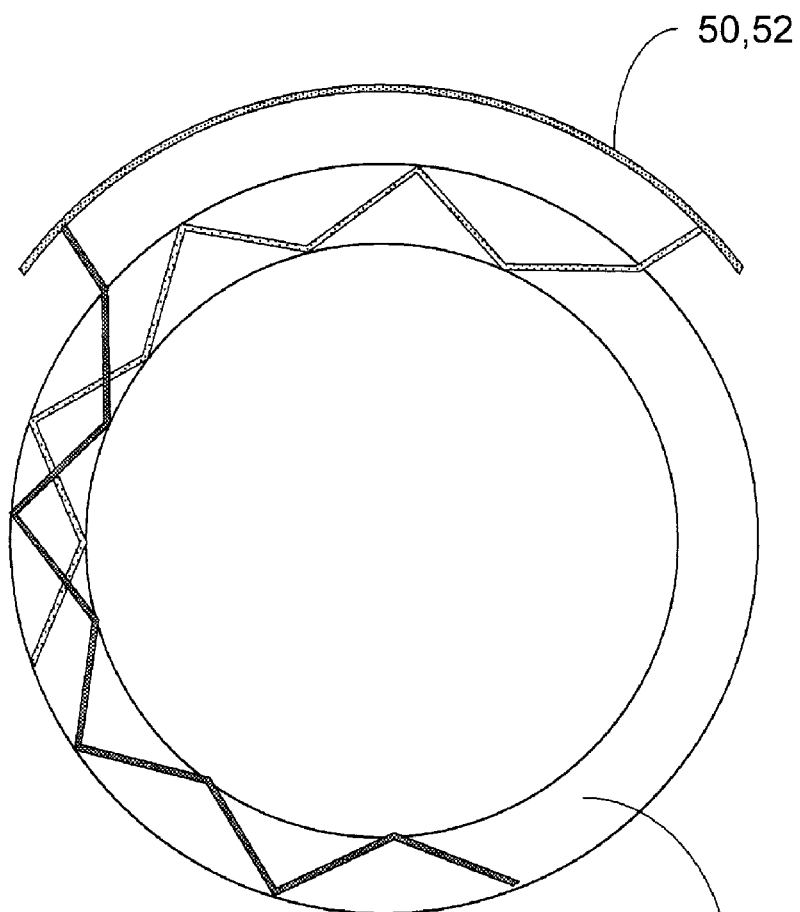
Figure 13:
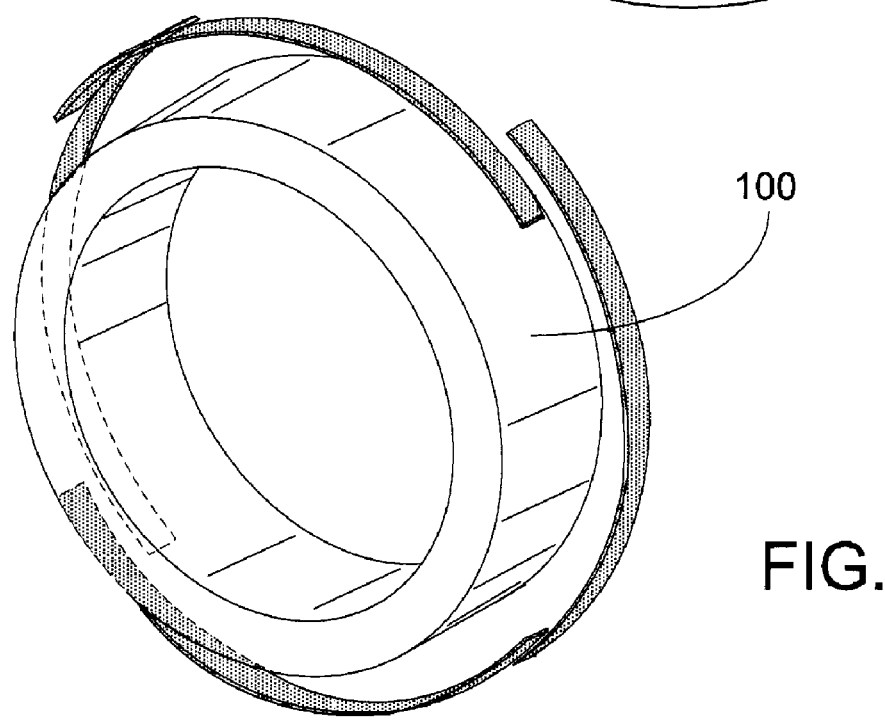

FIGS. 12 and 13 schematically illustrate how four overlapping UT transducer arrays in the probe 10 can be used for pipe inspection. UT signals are supplied to the transducers in a circular direction shown by the arrows in FIG. 12. The transducers can be provided in a 112/128 element array for 2" and 2.5" feeders respectively and driven at 5 MHz, other configurations and drive frequencies may be used. The mechanical probe design may thus be used and reused with different transducers. Immersion with 0.25" of water path and mechanical scanning in the axial direction at a maximum scan velocity of 2" per second along the pipe 100 to be tested is used. Electronic scanning in the circular direction is used and full coverage and multiple inspections in one pass are possible for axial cracking and for thickness variations. Axial cracking at up to 45 degrees shear from both directions, ID creeping wave and entire inspection volume coverage by one skip or less is possible. Zero degrees L wave and 0.1" spot size or better are also possible for thickness measurements.

Figure 14:
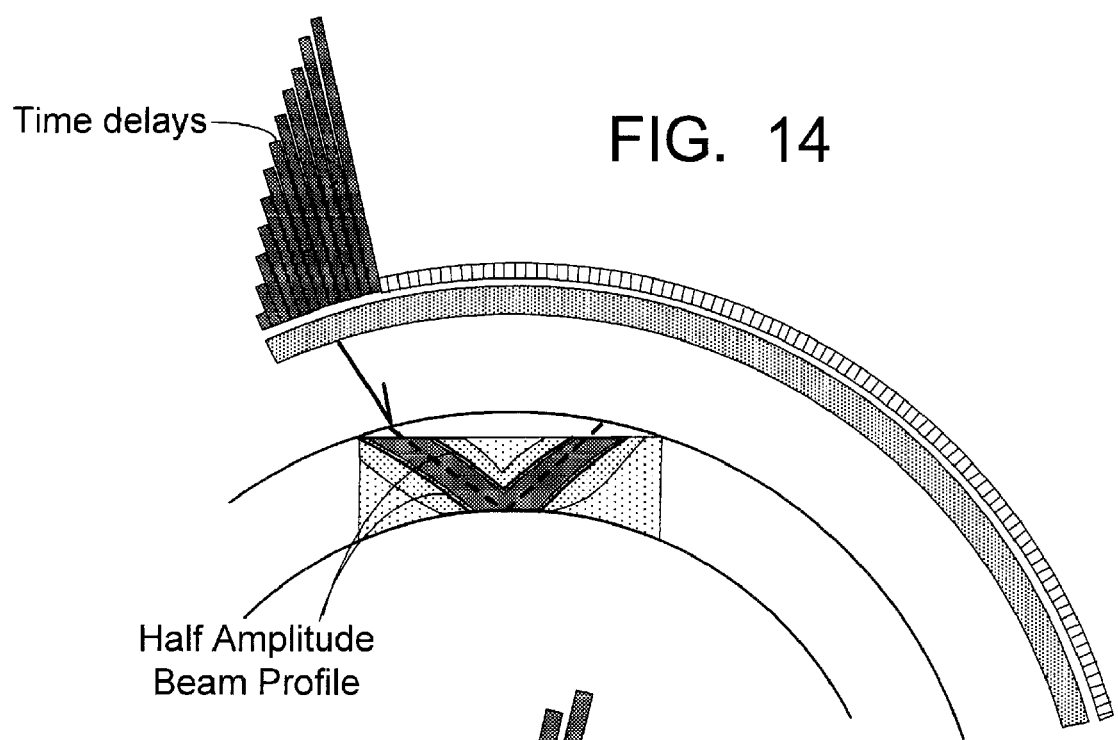
FIG. 14 is a conceptual diagram showing UT signal propagation in a pipe to be tested for axial cracks by the probe.
Figure 15:
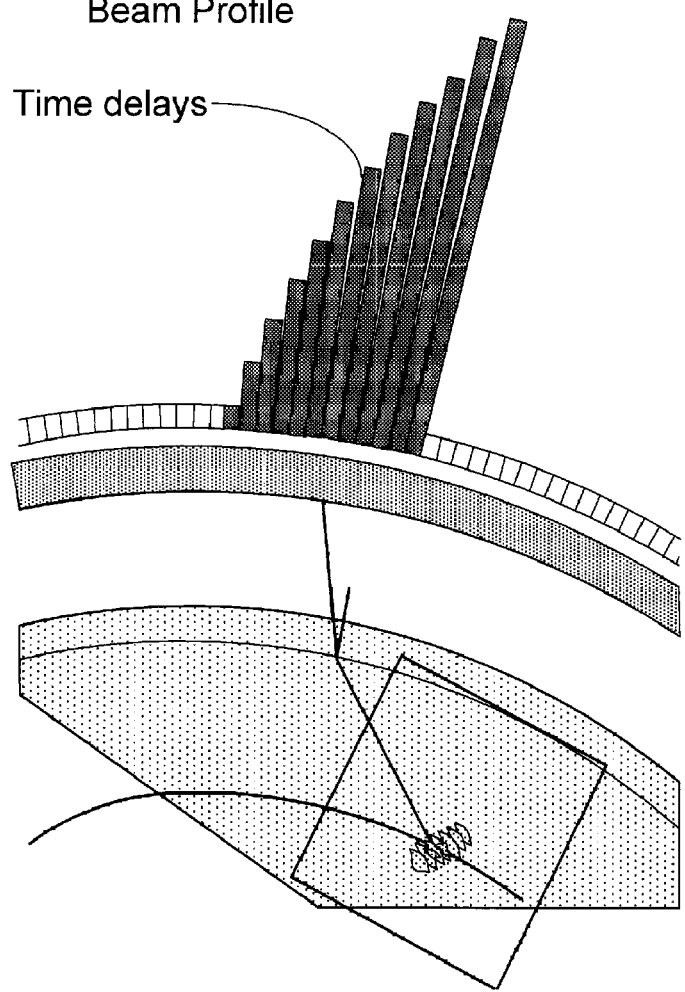
FIG. 15 is a conceptual diagram showing a simulated response to a 1 mm EDM notch on the inside diameter of the pipe being tested for axial cracks detected by the probe.
Figure 16:
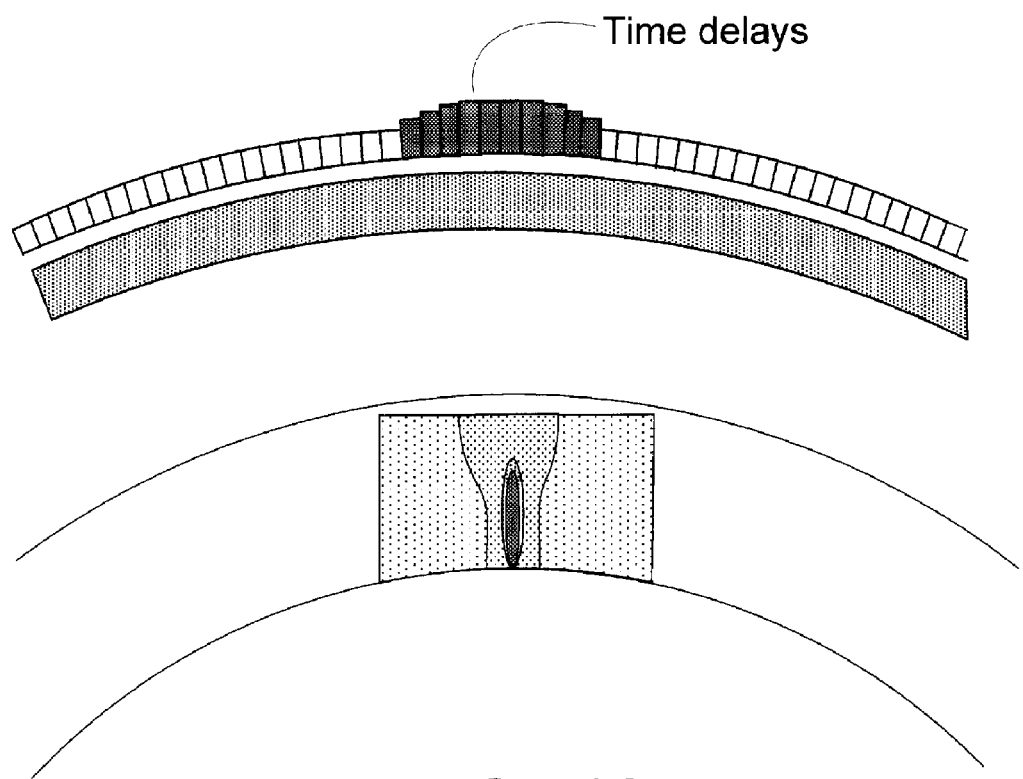
FIG. 16 is a conceptual diagram showing thickness mode measurements to a resolution of 1 mm using the probe.
Figure 17:
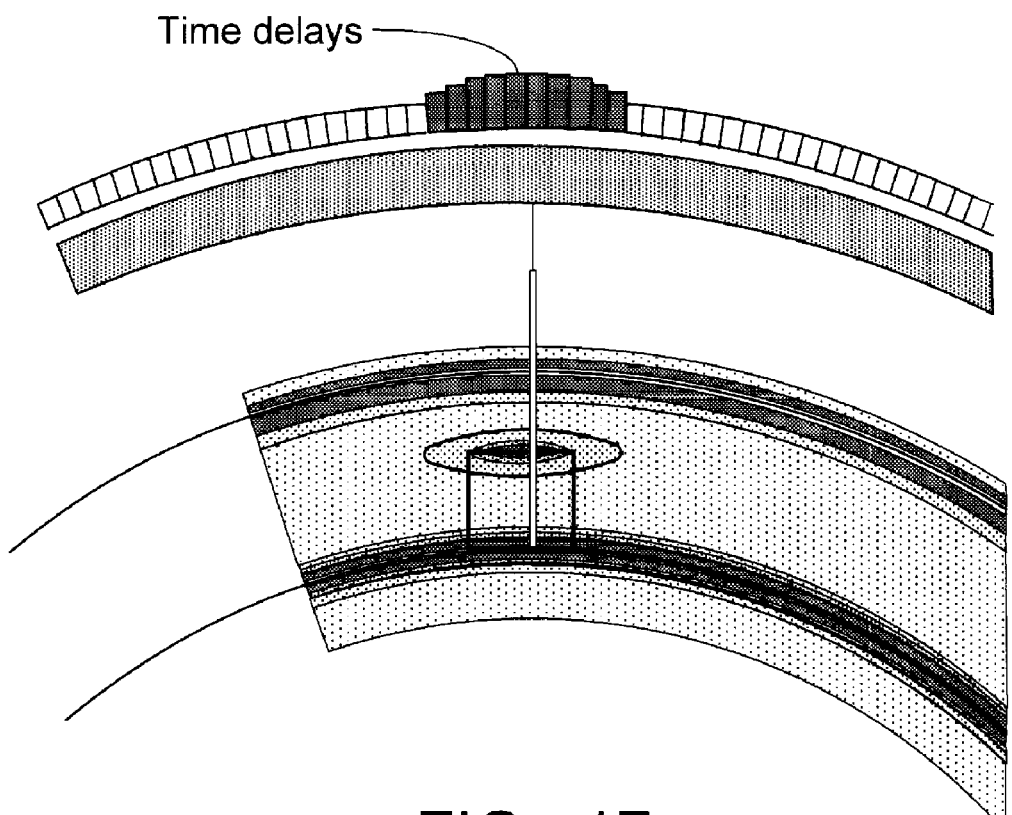
FIG. 17 is a conceptual diagram showing thickness mode measurements with response to a 3 mm diameter, flat-bottomed, 3 mm deep hole in the pipe wall, using the probe of the invention.

Simulations of axial crack detection are illustrated in FIGS. 14 and 15 and thickness mode operation is illustrated in FIGS. 16 and 17. FIGS. 14, 15, 16 and 17 are images modeling the use of the probe according to the present invention which were using CIVA simulation software (in this case, CIVA Version 9.0) for nondestructive testing modeling. CIVA simulation software is the result of more than fifteen years of development sponsored by the Commissariat à l'Énergie Atomique (CEA, the French Atomic Energy Commission), and is available in the United States from Bercli, 2813 Seventh Street, Berkeley, Calif. 94710, USA.

Figure 18:
FIG. 18 is a legend for FIGS. 14-17 identifying the amplitude ranges for the ultrasonic wave peak intensity or energy graphical shading representations in these Figures.
Figure 18:
Figure 18:
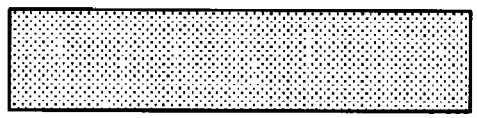
Figure 18:
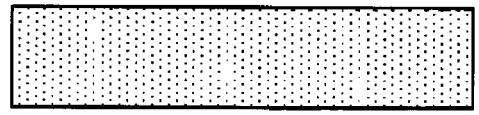

Finally, FIG. 18 is a legend for FIGS. 14-17 identifying the amplitude ranges for the ultrasonic wave peak intensity or energy graphical shading representations in these Figures.

The encircling array of the probe 10 provides 360 degree inspection for both thickness and cracking in a single pass. An axial scan rate of 2 inches per second is contemplated. Improved axial crack detection of the invention is provided by using a single skip to detect flaws opposed to 3.5 skips used by other techniques. Greatly increased scan rates by using electronic circumferential scanning is possible. Using the techniques disclosed in US Patent Application Publication US2008/0121040A1 to MacLauchlan et al., the text of which is hereby incorporated by reference as though fully set forth herein, the ultrasonic beam is also corrected for curved surfaces and data collection methodology provides for indication characterization without rescanning, greatly reducing personnel and dose requirements. Improved thickness measurements are also possible with overlapping thickness measurements in as little as 0.5 mm increments for complete coverage. This data collection methodology provides for enhanced wall thinning characterization without rescanning. Water-path measurement can be provided for actuator feedback and accurate surface profile can be provided in inspection results. Fewer scans are needed because both crack detection and thickness data is captured simultaneously for entire inspection volume in one pass.

Although a pair of pivotal jaws 32 is shown in the drawings, one of the jaws may be fixed to the base 30 and only the other jaw may be pivotal at its joint 34 for opening to admit a target component perimeter into the coupling chamber. In this case the sets of front and rear seals only need front and rear seals for the base and the single pivotal jaw as well as the joint surfaces and the side surface between the short and long sides of the jaw that have gasket seals and a slide surface seal for sealing the coupling chamber when the jaw is in its closed position.

Other alternatives that are also within the scope of the invention include the following: Brushes could be used as a seal instead of or in addition to an elastomer. Variations may be employed in the design of the electronic connections to reduce the overall profile. Various manual or automated features may be used to enhance the clamping action of the probe onto a pipe. For a lower profile design that maximizes water path, the transducer arrays could be arranged so that sound is transmitted parallel to the axis of the pipe. An ultrasonic mirror could then be used to redirect the beam into the pipe.

The probe 10 according to the present invention has a pipe-encircling, low profile configuration for the onsite UT inspection of pipes or other target components that can be encircled by the probe. The clamshell, hinged design provides this low profile for much of the probe 10 which allows the probe to inspect piping with limited clearance, for example, CANDU feeder pipes typically having only 0.5" to 2.0" of clearance in the radial direction. For example, the main portion of the probe 10 illustrated in FIGS. 6 and 7 has a height of less than about 5 inches, a width less than about 3¾ inches and a thickness (excluding the shoulder bolts at the joints 34) of about 1 inch.

While a specific embodiment of the invention has been shown and described in detail to illustrate the application of the principles of the invention, it will be understood that the invention may be embodied otherwise without departing from such principles.

What is claimed is:

1. An ultrasonic probe for encircling the perimeter of a target component to be ultrasonically tested, the probe comprising:
   a base having a first arcuate inner surface for partly encircling a target component perimeter;
   a pair of jaws pivotally mounted to the base at respective opposite ends of the first arcuate inner surface, at a pair of respective joints, said jaws having respective second and third arcuate inner surfaces each for partly encircling a target component perimeter, said jaws having a closed position wherein the first, second and third arcuate inner surfaces form a continuous closed loop for encircling a target component perimeter, and an open position for admitting a target component between the jaws;
   a set of front seals connected to and extending along a front portion of the first, second and third arcuate inner surfaces for forming a continuous front seal for sealing engagement against a target component perimeter in the closed position of the jaws;
   a set of rear seals connected to and extending along a rear portion of the first, second and third arcuate inner surfaces for forming a continuous rear seal for sealing engagement against a target component perimeter in the closed position of the jaws;

said front and rear seals being spaced from each other to form an annular coupling fluid chamber between the arcuate inner surfaces and an outer surface of a target component perimeter when a target component is encircled by the arcuate inner surfaces and the jaws are in their closed position;

the base having at least one coupling fluid passage opening into the first arcuate inner surface for supplying coupling fluid into the coupling fluid chamber;

an arcuate set of ultrasonic transducers connected along at least one of the arcuate inner surfaces for transmitting ultrasonic signals to the coupling fluid chamber; and a circuit connected to each set of ultrasonic transducers for electrically connecting each set of ultrasonic transducers to ultrasonic processing electronics for ultrasonically testing a target component.

2. The ultrasonic probe of claim 1, wherein each jaw has a short arcuate side and a long arcuate side spaced one of forwardly and rearwardly of the short arcuate side, the sets of front and rear seals each including respective short and long seals extending along the arcuate inner surfaces of the jaws and on the short and long sides of the jaws.

3. The ultrasonic probe of claim 1, wherein each jaw has a short arcuate side and a long arcuate side spaced one of forwardly and rearwardly of the short arcuate side, the sets of front and rear seals each including respective short and long seals extending along the arcuate inner surfaces of the jaws and on the short and long sides of the jaws, each set of front and rear seals including gasket seals at each of the joints.

4. The ultrasonic probe of claim 1, wherein each set of front and rear seals include gasket seals at each of the joints.

5. The ultrasonic probe of claim 1, wherein each jaw has a short arcuate side and a long arcuate side spaced one of forwardly and rearwardly of the short arcuate side, the sets of front and rear seals each including respective short and long seals extending along the arcuate inner surfaces of the jaws and on the short and long sides of the jaws, each short side of each jaw being spaced from a respective joint so that a joint surface of each short side and an adjacent joint surface of the base become spaced apart when each jaw is in its open position, each set of front and rear seals including gasket seals on each joint surface for sealing the joint surfaced to each other when the jaws are in their closed positions.

6. The ultrasonic probe of claim 1, wherein each jaw has a short arcuate side and a long arcuate side spaced one of forwardly and rearwardly of the short arcuate side, the sets of front and rear seals each including respective short and long seals extending along the arcuate inner surfaces of the jaws and on the short and long sides of the jaws, each short side of each jaw being spaced from a respective joint so that a joint surface of each short side and an adjacent joint surface of the base become spaced apart when each jaw is in its open position, each set of front and rear seals including gasket seals on each joint surface for sealing the joint surfaced to each other when the jaws are in their closed positions, each joint including a side surface between the short and long sides of each respective jaw and a slide surface seal on each side surface.

7. The ultrasonic probe of claim 1, wherein each jaw has a short arcuate side and a long arcuate side spaced one of forwardly and rearwardly of the short arcuate side, the sets of front and rear seals each including respective short and long seals extending along the arcuate inner surfaces of the jaws and on the short and long sides of the jaws, the short sides of each jaw being spaced circumferentially from both ends of the long sides of each jaw.

8. The ultrasonic probe of claim 1, wherein each arcuate inner surface is a segment of a circle.

9. The ultrasonic probe of claim 1, wherein the base includes a pair of coupling fluid passages opening into the first arcuate inner surface for supplying coupling fluid into the coupling fluid chamber.

10. An ultrasonic probe for encircling the perimeter of a target component to be ultrasonically tested, the probe comprising:

a base having a first arcuate inner surface for partly encircling a target component perimeter;

at least one jaw pivotally mounted to the base at one end of the first arcuate inner surface, at a joint, said jaw having a second arcuate inner surface for partly encircling a target component perimeter, said jaw having a closed position wherein the first and second arcuate inner surfaces form a continuous closed loop for encircling a target component perimeter, and an open position for admitting a target component between the jaw and the base;

a set of front seals connected to and extending along a front portion of the first and second arcuate inner surfaces for forming a continuous front seal for sealing engagement against a target component perimeter in the closed position of the jaw;

a set of rear seals connected to and extending along a rear portion of the first and second arcuate inner surfaces for forming a continuous rear seal for sealing engagement against a target component perimeter in the closed position of the jaw;

said front and rear seals being spaced from each other to form an annular coupling fluid chamber between the arcuate inner surfaces and an outer surface of a target component perimeter when a target component is encircled by the arcuate inner surface and the jaw is in its closed position;

the base having at least one coupling fluid passage opening into the first arcuate inner surface for supplying coupling fluid into the coupling fluid chamber;

an arcuate set of ultrasonic transducers connected along at least one of the arcuate inner surfaces for transmitting ultrasonic signals to the coupling fluid chamber; and a circuit connected to each set of ultrasonic transducers for electrically connecting each set of ultrasonic transducers to ultrasonic processing electronics for ultrasonically testing a target component.

11. The ultrasonic probe of claim 10, wherein the jaw has a short arcuate side and a long arcuate side spaced one of forwardly and rearwardly of the short arcuate side, the sets of front and rear seals each including respective short and long seals extending along the arcuate inner surface of the jaw and on the short and long sides of the jaw.

12. The ultrasonic probe of claim 10, wherein the jaw has a short arcuate side and a long arcuate side spaced one of forwardly and rearwardly of the short arcuate side, the sets of front and rear seals each including respective short and long seals extending along the arcuate inner surface of the jaw and on the short and long sides of the jaw, each set of front and rear seals including gasket seals for the joint.

13. The ultrasonic probe of claim 10, wherein each set of front and rear seals include gasket seals at the joint.

14. The ultrasonic probe of claim 10, wherein the jaw has a short arcuate side and a long arcuate side spaced one of forwardly and rearwardly of the short arcuate side, the sets of front and rear seals each including respective short and long seals extending along the arcuate inner surface of the jaw and on the short and long sides of the jaw, the short side of the jaw being spaced from the joint so that a joint surface of the short side and an adjacent joint surface of the base become spaced apart when the jaw is in its open position, each set of front and rear seals including gasket seals on each joint surface for sealing the joint surfaced to each other when the jaw is in its closed position.

15. The ultrasonic probe of claim 10, wherein the jaw has a short arcuate side and a long arcuate side spaced one of forwardly and rearwardly of the short arcuate side, the sets of front and rear seals each including respective short and long seals extending along the arcuate inner surface of the jaw and on the short and long sides of the jaw, each short side of the jaw being spaced from the joint so that a joint surface of the short side and an adjacent joint surface of the base become spaced apart when the jaw is in its open position, each set of front and rear seals including gasket seals on the joint surface for sealing the joint surface to each other when the jaw is in its closed position, the joint including a side surface between the short and long sides of the jaw at the joint and a slide surface seal on the side surface.

16. The ultrasonic probe of claim 10, wherein the jaw has a short arcuate side and a long arcuate side spaced one of forwardly and rearwardly of the short arcuate side, the sets of front and rear seals each including respective short and long seals extending along the arcuate inner surfaces of the jaw and on the short and long sides of the jaw, the short side of the jaw being spaced circumferentially for both ends of the long sides of the jaw.

17. The ultrasonic probe of claim 10, wherein each arcuate inner surface is a segment of a circle.

18. The ultrasonic probe of claim 10, wherein the base includes a pair of coupling fluid passages opening into the first arcuate inner surface for respectively supplying and withdrawing coupling fluid into and out of the coupling fluid chamber.

19. An ultrasonic probe for encircling the perimeter of a target component to be ultrasonically tested, the probe comprising:
　　a base having a first arcuate inner surface for partly encircling a target component perimeter;
　　a pair of jaws pivotally mounted to the base at respective opposite ends of the first arcuate inner surface, at a pair of respective joints, said jaws having respective second and third arcuate inner surfaces each for partly encircling a target component perimeter, said jaws having a closed position wherein the first, second and third arcuate inner surfaces form a continuous closed loop for encircling a target component perimeter, and an open position for admitting a target component between the jaws;
　　a set of front seals connected to and extending along a front portion of the first, second and third arcuate inner surfaces for forming a continuous front seal for sealing engagement against a target component perimeter in the closed position of the jaws;
　　a set of rear seals connected to and extending along a rear portion of the first, second and third arcuate inner surfaces for forming a continuous rear seal for sealing engagement against a target component perimeter in the closed position of the jaws;
　　said front and rear seals being spaced from each other to form an annular coupling fluid chamber between the arcuate inner surfaces and an outer surface of a target component perimeter when a target component is encircled by the arcuate inner surface and the jaws are in their closed position;
　　the base having at least one coupling fluid passage opening into the first arcuate inner surface for supplying coupling fluid into the coupling fluid chamber;
　　an arcuate set of ultrasonic transducers connected along at least one of the arcuate inner surfaces for transmitting ultrasonic signals to the coupling fluid chamber; and
　　a circuit connected to each set of ultrasonic transducers for electrically connecting each set of ultrasonic transducers to ultrasonic processing electronics for ultrasonically testing a target component;
　　each jaw having a short arcuate side and a long arcuate side spaced one of forwardly and rearwardly of the short arcuate side, the sets of front and rear seals each including respective short and long seals extending along the arcuate inner surfaces of the jaws and on the short and long sides of the jaws.

20. The ultrasonic probe of claim 19, wherein each set of front and rear seals includes gasket seals at each of the joints and a slide seal on a surface between the short and long sides of each jaw adjacent each joint.

* * * * *